United States Patent

Suzuki et al.

Patent Number: 5,219,864
Date of Patent: Jun. 15, 1993

[54] THIENOPYRIDINE DERIVATIVES

[75] Inventors: Fumio Suzuki, Mishima; Yoshikazu Miwa, Shizuoka; Hiroaki Hayashi, Shizuoka; Takeshi Kuroda, Shizuoka; Kenji Ohmori, Mishima; Hiroshi Nakajima, Shizuoka, all of Japan

[73] Assignee: Kyowa Hakko Kogyo Co., Ltd., Tokyo, Japan

[21] Appl. No.: 847,665

[22] Filed: Mar. 4, 1992

[30] Foreign Application Priority Data

Mar. 12, 1991 [JP] Japan ................... 46267/91

[51] Int. Cl.$^5$ ............... C07D 491/048; A61K 31/44
[52] U.S. Cl. ..................................... 514/301; 546/114
[58] Field of Search ...................... 546/114; 514/301

[56] References Cited

U.S. PATENT DOCUMENTS

| | | | |
|---|---|---|---|
| 4,499,094 | 2/1985 | Dubroeucg et al. | 514/301 |
| 4,877,793 | 10/1989 | Davies | 514/301 |

FOREIGN PATENT DOCUMENTS

| | | |
|---|---|---|
| 0059698 | 9/1982 | European Pat. Off. |
| 0094271 | 11/1983 | European Pat. Off. |
| 0452873 | 10/1991 | European Pat. Off. |

OTHER PUBLICATIONS

Barker et al., J. Chem. Research, No. 6 (1982) 158.
Barker et al., J. Chem. Research, No. 7 (1985) 214:5.

*Primary Examiner*—C. Warren Ivy
*Assistant Examiner*—Barbara Twardzik
*Attorney, Agent, or Firm*—Fitzpatrick, Cella, Harper & Scinto

[57] ABSTRACT

Disclosed is a thienopyridine derivative represented by formula (I):

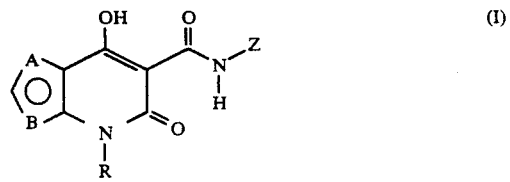

wherein one of A and B represents —S— and the other represents —CH=; R represents hydrogen or lower alkyl, and Z represents pyridyl; or a pharmaceutically acceptable salt thereof.

The thienopyridine derivative is useful as an immunoregulator and for the prevention and treatment of osteoporosis.

5 Claims, No Drawings

THIENOPYRIDINE DERIVATIVES

BACKGROUND OF THE INVENTION

The present invention relates to thienopyridine derivatives which are useful as an immunoregulator and for the prevention and treatment of osteoporosis.

Thienopyridine derivatives represented by Formula (A), possess the 4-hydroxythieno[2,3-b]pyridin-6-one skeleton and are described in J. Chem. Res. (S), 214 (1985) and J. Chem. Res. (S), 122 (1986):

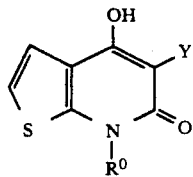

wherein R° represents hydrogen or methyl and Y represents hydrogen or ethoxycarbonyl.

Furthermore, thienopyridine derivatives represented by Formula (B), possess the 7-hydroxythieno[3,2-b]-pyridin-5-one skeleton, and are described in J. Chem. Res. (S), 6 (1980) and J. Chem. Res. (S), 84 (1984):

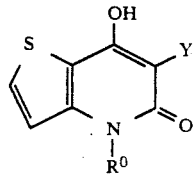

wherein R° represents hydrogen or methyl and Y represents hydrogen, ethoxycarbonyl, nitrile, acetyl or the like.

In compounds (A) and (B), their pharmacological acitivities are unknown.

SUMMARY OF THE INVENTION

The present invention relates to thienopyridine derivatives [hereinafter referred to as Compound (I)] represented by formula (I):

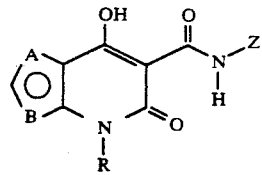

wherein one of A and B represents -S-, and the other represent —CH=; R represents hydrogen or lower alkyl, and Z represents pyridyl; or a pharmaceutically acceptable salt thereof.

DETAILED DESCRIPTION OF THE INVENTION

In the definition of each group in formula (I), the lower alkyl means a straight or branched alkyl having 1 to 6 carbon atoms, such as methyl, ethyl, propyl, isopropyl, butyl, isobutyl, sec-butyl, tert-butyl, pentyl, neopentyl, hexyl, etc.

The pharmaceutically acceptable salt of Compound (I) includes acid addition salts, metal salts, etc. The acid addition salt includes, for example, an inorganic acid salt such as hydrochloride, sulfate, phosphate, etc.; an organic acid salt such as acetate, maleate, fumarate, tartarate, citrate, etc. The metal salt includes for example, salts of alkali metal such as sodium, potassium, etc., salts of alkaline earth metal such as magnesium, calcium, etc.; aluminum salts, zinc salts and the like.

Next, a process for preparing Compound (I) is described.

In the process shown below, in cases where the defined group(s) change under the conditions or are inappropriate for the practice of the process, the process can be easily operated by applying thereto means conventionally used in organic synthetic chemistry, for example, protection of functional groups, removal of protective groups, etc.

Compound (I) may be obtained by reacting Compound (III) represented by formula (II):

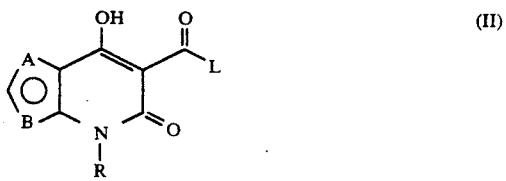

wherein L represents a leaving group; and A, B and R have the same significance as described above, with Compound (III) represented by formulas (III):

$$H_2N—X \qquad (III)$$

wherein X has the same significance as described above, preferably in the presence of a base.

Herein as the leaving group denoted by L, halogen such as chlorine, bromine, iodine, etc.; alkoxy such as methoxy, ethoxy, etc.; aryloxy such as phenoxy, etc.; alkanoyloxy such as propionyloxy, etc.; aroyloxy such as benzoyloxy, etc. are used.

As the base, alkali metal bicarbonates such as sodium bicarbonate, potassium bicarbonate, etc.; alkali metal carbonates such as sodium carbonate, potassium carbonate, etc.; alkali metal hydrides such as sodium hydride, etc.; alkali metal alkoxides such as sodium methoxide, sodium ethoxide, etc.; alkali metal salts such as butyl lithium, etc. are used.

As the solvent used in the reaction, any solvent may be usable, as long as it is inert to the reaction. For example, ethers such as tetrahydrofuran, dioxane, etc.; amides such as dimethylformamide, dimethylacetamide, etc.; ketones such as acetone, methyl ethyl ketone, etc.; alcohols such as methanol, ethanol, isopropyl alcohol, etc.; halogenated hydrocarbons such as methylene chloride, chloroform, dichloroethane, etc.; esters such as ethyl acetate, etc.; aromatic hydrocarbons such as benzene, toluene, xylene, etc.; dimethylsulfoxide and the like may be used singly or in combination.

The reaction is carried out at −30° to 200° C., preferably −10° to 100° C. and generally completed in 30 minutes to 20 hours.

The starting compound (II) can be synthesized by known methods [J. Chem. Res. (S), 6 (1980); ibid., 84 (1984); ibid., 214 (1985); J. Chem. Res. (M), 113 (1980); ibid., 771 (1984); ibid., 2501 (1985)] or by a modified method of these methods.

The desired product in the process described above can be isolated and purified by means of purification conventionally used in organic synthetic chemistry, for example, by filtration, extraction, washing, drying, concentration, recrystallization, various chromatographies, etc.

Where it is desired to obtain the salts of Compound (I), Compound (I) may be purified as it is in case that Compound (I) is obtained in the form of its salt. In case that Compound (I) is obtained in its free form, Compound (I) is dissolved or suspended in a appropriate solvent and an appropriate acid or base is added to the solution or suspension to form its salts.

Compound (I) and a pharmaceutically acceptable salt thereof may also be present int he form of addition products with water or various solvents. These addition products are also included in the present invention.

Furthermore Compound (I) includes all possible steric isomers and mixtures thereof.

Specific examples of Compound (I) obtained by the process described above are shown in Tables 1 and 2.

TABLE 1

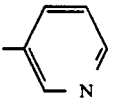

| Compound No. | R | Z |
| --- | --- | --- |
| 1 | H | 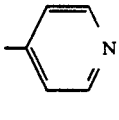 |
| 2 | H | 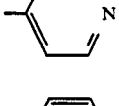 |
| 3 | $(CH_2)_3CH_3$ | 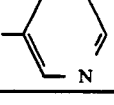 |
| 4 | $(CH_2)_3CH_3$ | 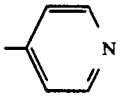 |

TABLE 2

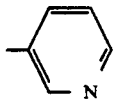

| Compound No. | R | Z |
| --- | --- | --- |
| 5 | $(CH_2)_3CH_3$ | 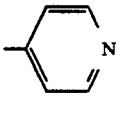 |

TABLE 2-continued

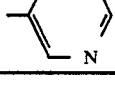

| Compound No. | R | Z |
| --- | --- | --- |
| 6 | $(CH_2)_3CH_3$ | |
| 7 | H | |
| 8 | H | |

Next, the immunoregulating activity, activity of inhibiting bone absorption and acute toxicity of Compound (I) are described by referring to test examples.

TEST EXAMPLE 1 Plaque Forming Cell Assay

The method developed by Jerne [Science, 140, 405 (1963)] and Yamamoto, et al [Drugs. Exptl. Clin. res., 8, 5 (1982)] were modified for plaque forming cell assay.

That is, Balb/c strain male mice (age of 7 weeks, Charles River Japan Inc.) were sensitized with $1 \times 10^8$ sheep red blood cells (Bio Test Research Institute) and the spleen was extirpated on the sixth or seventh day. The cells obtained from the spleen were treated with ACT solution (Tris-ammonium chloride isotonic buffer) to remove red blood cells. The cells were washed three times with RPMI-1640 medium (Nissui Pharmaceutical Co. . The cells ($1 \times 10^7$) were incubated in RPMI-1640 medium containing 10% calf fetal serum (Gibco Co.), 50 μg/ml streptomycin, 50 IU/ml of penicillin, 2-mercaptoethanol ($5 \times 10^{-5}$ M), sheep red blood cells ($5 \times 10^6$ cells) and a test compound dissolved in dimethyl sulfoxide supplied on a microculture plate (NUNC Co., 24 wells) in a carbon dioxide gas incubator (TABAI ESPEC CORP) at 37° C. for 5 days.

After completion of the incubation, the cells were transferred to a plastic test tube and centrifuged at 2000 rpm. After the supernatant was removed, the cells were resuspended in 1 ml of RPMI-1640 medium. The cell suspension was sealed in a Cunnigham chamber (Takahashi Giken Co.) together with sheep red blood cells and guinea pig complement (Cedarlane Research Institute) according to the method of Cunnigham [Immunology, 14, 599 (1968)] and incubated at 37° C. for 1 to 2 hours. Direct plaque forming cell (PFC) count was counted.

A rate of inhibiting antibody production by the test compound was determined by the following equation.

$$\text{Inhibition rate (\%)} = \frac{A - B}{A} \times 100$$

A : PFC count in the absence of test compound (dimethylsulfoxide alone)
B : PFC count in the presence of test compound
The results are shown in Table 3.

TABLE 3

| Compound No. | Concentration (M) | Direct PFC Count (mean ± S.E.M.) | Inhibition Rate (%) |
|---|---|---|---|
| Control |  | 5023 ± 38 |  |
| 3 | $10^{-4}$ | 101 ± 76 | 98.0 |
|  | $10^{-5}$ | 59 ± 38 | 98.8 |
| 4 | $10^{-4}$ | 336 ± 124 | 93.3 |
|  | $10^{-5}$ | 395 ± 52 | 92.1 |
| 5 | $10^{-4}$ | 109 ± 77 | 97.8 |
|  | $10^{-5}$ | 227 ± 131 | 95.5 |
| 6 | $10^{-4}$ | 42 ± 29 | 99.2 |
|  | $10^{-5}$ | 59 ± 29 | 98.8 |

Autoimmune diseases such as chronic articular rheumatism or the like are considered to result from tissue injury due to accentuation of B cells as the result of hypofunction of T cells. It is thus expected that Compound (I) would be effective against autoimmune disease by inhibiting antibody production.

TEST EXAMPLE 2 Activity of inhibiting bone absorption

A calvaria of a 5 to 6 day-old dd mouse was aseptically cut off, washed with Dulbecco's modified phosphate buffered saline not containing calcium and magnesium (manufactured by Gibco Oriental Co.) and separated along the sutura of its center. One half of the calvaria so separated was cultured in 1.5 ml of Dulbecco's modified Eagle medium (manufactured by Gibco Oriental Co.) containing 15% of thermally inactivated (at 56° C. for 20 minutes) horse serum and 2.5% of fetal calf serum. The test compound was dissolved in dimethyl sulfoxide, and 10 μl (final concentration: $1 \times 10^{-4}$ M or $1 \times 10^{-5}$ M) of the solution so prepared was added to the culture. Parathyroid hormone (human PTH 1-34, manufactured by Sigma Co.) was dissolved in 0.15 M sodium chloride solution (pH 3), and 3 μl (final concentration: $1 \times 10^{-8}$ M) of the solution so prepared was added to the culture. The cultivation was carried out for 96 hours at 37° C. in an atmosphere consisting of 95% of air and 5% of carbon dioxide. The culture medium was once replaced with a fresh one after 48 hours from the beginning of the cultivation. The concentration of dissolved calcium (i.e., absorption of bone) from the PTH-intensified bone was determined by measuring the quantity of calcium accumulated in the culture collected in 96 hours of cultivation, whereby the concentration of total calcium contained in the culture was measured with Calcium C-Test Wako (manufactured by Wako Pure Chemicals Co., Ltd.), and the inhibition rate was calculated therefrom in accordance with the equation set forth below. The results are shown in Table 4.

$$\text{Inhibition rate (\%)} = \frac{Cp - Cd}{Cp - Co} \times 100$$

Cd : Total calcium concentration in the culture treated with both test compound and PTH
Cp : Total calcium concentration in the culture treated with PTH alone
Co Total calcium concentration in the culture treated with neither test compound nor PTH

TABLE 4

| Compound No. | Concentration (μM) | Inhibition Rate (%) |
|---|---|---|
| 1 | 100 | −1 |
| 2 | 100 | 51 |
| 3 | 10 | 141 |
| 4 | 10 | 58 |
| 5 | 10 | 53 |
| 6 | 10 | 38 |
| 7 | 10 | 32 |
| 8 | 10 | 18 |

TEST EXAMPLE 3 Acute toxicity test

A test compound was orally administered to three dd-strain male mice weighting 20±1 g. The minimum lethal dose (MLD) was determined by observing the mortality for 7 days after the administration.
The results are shown in Table 5.

TABLE 5

| Compound No. | MLD (mg/kg) |
|---|---|
| 4 | >300 |
| 7 | >300 |

Compound (I) or a pharmaceutically acceptable salt thereof may be used as it is, or in various pharmaceutical forms. The pharmaceutical composition of the present invention can be prepared by uniformly mixing an effective amount of Compound (I) or a pharmaceutically acceptable salt thereof as the active ingredient with pharmaceutically acceptable carriers. The pharmaceutical compositions are desirably in a single dose unit suited for oral or parenteral administration.

In preparing the composition suited for oral administration, any pharmaceutically acceptable carrier may be used. Liquid preparations suited for oral administration, for example, a suspension and a syrup can be prepared using water; sugars such as sucrose, sorbitol, fructose, etc.; glycols such as polyethylene glycol, propylene glycol, etc.; oils such as sesame oil, olive oil, soybean oil, etc.; antiseptics such as p-hydroxybenzoic acid ester, etc.; flavors such as strawberry flavor, pepper mint, etc. Further a capsule, a tablet, a powder and a granule can be prepared using an excipient such as lactose, glucose, sucrose, mannitol, etc.; a disintegrator such as starch, sodium alginate, etc.; a lubricant such as magnesium stearate, talc, etc.; a binder such as polyvinyl alcohol, hydroxypropyl cellulose, gelatin, etc.; a surfactant such as a fatty acid ester, etc.; a plasticizer such as glycerine, etc. A tablet and a capsule are most useful single dose unit for oral administration because their administration is easy.

Effective dose and number of administration of Compound (I) or a pharmaceutically acceptable salt thereof may vary depending upon modes of administration, age and body weight, conditions, etc. of a patient but it is generally preferred to administer Compound (I) in a dose of 1 to 1,000 mg/60 kg by dividing into one to four times.

The present invention is described by referring to Examples and Reference Examples below.

EXAMPLE 1
4,5-Dihydro-7-hydroxy-5-oxo-N-(3-pyridyl)thieno[3,2-b]-pyridine-6-carboxamide (Compound 1)

A mixture of 2.43 g (10.2 mmols) of ethyl 4,5-dihydro-7-hydroxy-5-oxothieno[3,2-b]pyridine-6-carboxylate [J. Chem. Res. (S), 6 (1980); J. Chem. Res. (M), 113 (1980)], 1.00 g (10.6 mmols) of 3-aminopyridine, 50 ml of xylene and 10 ml of dimethylformamide was heated at 140° C. for an hour. After completion of the reaction, insoluble matters were filtered and recrystallized from dimethylformamide to give 1.56 g (yield: 54%) of Compound 1.

Elemental analysis: $C_{13}H_9N_3O_3S$:
Calcd. (%): C 54.35, H 3.16, N 14.63
Found (%) : C 54.11, H 2.85, N 14.48
IR (KBr) cm$^{-1}$: 3450(br), 1638, 1594, 1547, 1480, 1408, 1364, 1264, 1228, 799, 761
NMR (CF$_3$ CO$_2$ D) δ(ppm): 9.79(1H, s), 8.81(1H, d, J=8.8Hz), 8.63(1H, d, J=5.1Hz), 8.15(1H, m), 8.10 (1H, d, J=5.4Hz), 7.28(1H, d, J=5.4Hz)

EXAMPLE 2
4,5-Dihydro-7-hydroxy-5-oxo-N-(4-pyridyl)thieno[3,2-b]-pyridine-6-carboxamide (Compound 2)

A mixture of 2.48 g (10.4 mmols) of ethyl 4,5-dihydro-7-hydroxy-5-oxothieno[3,2-b]pyridine-6-carboxylate [J. Chem. Res. (S), 6 (1980); J. Chem. Res. (M), 113 (1980)], 1.01 g (10.7 mmols) of 4-aminopyridine, 50 ml of xylene and 10 ml of dimethylformamide was heated at 140° C. for an hour. After completion of the reaction, insoluble matters were filtered and tritylated with dimethylformamide with heating to give 1.99 g (yield: 67%) of Compound 2.

Elemental analysis: $C_{13}H_9N_3O_3S$
Calcd. (%): C 54.35, H 3.16, N 14.63
Found (%): C 54.31, H 2.96, N 14.45
IR (KBr) cm$^{-1}$: 3440(br), 1662, 1632, 1575, 1536, 1498, 1411, 1370, 1212, 1006, 826, 751
NMR (CF$_3$ CO$_2$ D) δ(ppm): 8.64(2H, d, J=7.0Hz), 8.46 (2H, d, J=7.0Hz), 8.11(1H, d, J=5.4Hz), 7.27(1H, d, J=5.4Hz)

EXAMPLE 3
4-(n-Butyl)-4,5-dihydro-7-hydroxy-5-oxo-N-(4-pyridyl)thieno-[3,2-b]pyridine-6-carboxamide (Compound 3)

A solution of 1.18 g (4.00 mmols) of the Compound a obtained in Reference Example 1, 0.39 g (4.13 mmols) of 4-aminopyridine and 20 ml of toluene was heated to reflux for 2 hours. After cooling, the reaction mixture was poured into 1 N sodium hydroxide aqueous solution, and washed twice with chloroform. 2 N Hydrochloric acid aqueous solution was added to the aqueous layer and the precipitated white crystals were filtered and dried to give 0.73 g (yield: 53%) of Compound 3.
Melting point: 211.9–216.5° C.
MS (EI) m/e: 343 (M+)
IR (KBr) cm$^{-1}$: 3420(br), 1661, 1617, 1591, 1546, 1509, 1393, 1196, 796, 758
NMR (DMSO-d$_6$) δ(ppm) 13.59(1H, s), 8.79(2H, d, J=6.6Hz), 8.38(1H, d, J=5.1Hz), 8.21(2H, d, J=6.6Hz), 7.57(1H, d, J=5.1Hz), 4.24(2H, t, J=7.6Hz), 1.66(2H, m), 1.40(2H, m), 0.93(3H, t, J=7.1Hz)

EXAMPLE 4
4-(n-Butyl)-4,5-dihydro-7-hydroxy-5-oxo-N-(3-pyridyl)thieno-[3,2-b]pyridine-6-carboxamide (Compound 4)

Compound 4 was obtained (yield: 72%) in a manner similar to Example 3 except for using 3-aminopyridine in place of 4-aminopyridine.
Melting point 179.7°–182.6° C.
MS (EI) m/e: 343 (M+)
IR (KBr) cm$^{-1}$: 3388, 1627, 1540, 1390, 798, 770, 668
NMR (DMSO-d$_6$) δ(ppm): 13.03(1H, s), 9.20[1H, d, J=2.2Hz), 8.62(1H, d, J=4.4Hz), 8.57(1H, dd, J=2.2Hz, 8.5Hz), 8.34(1H, d, J=5.4Hz), 7.90(1H, dd, J=4.4Hz, 8.5Hz), 7.55(1H, d, J=5.4Hz), 4.24(2H, t, J=7.5Hz), 1.65(2H, m), 1.40(2H, m), 0.93(3H, t, J=7.3Hz)

EXAMPLE 5
7-(n-Butyl)-6,7-dihydro-4-hydroxy-6-oxo-N-(4-pyridyl)thieno-[2,3-b]pyridine-5-carboxamide (Compound 5)

Compound 5 was obtained (yield: 78%) in a manner similar to Example 3 except for using Compound b obtained in Reference Example 2 in place of Compound a.
Melting point: 131.6°–139.4° C.
MS (EI) m/e: 343 (M+)
IR (KBr) cm$^{-1}$: 2952, 1614, 1507, 1380, 1289, 1197, 834, 663
NMR (DMSO-d$_6$) δ(ppm): 13.34(1H, s), 8.78(2H, d, J=6.4Hz), 8.20(2H, d, J=6.4Hz), 7.48(1H, d, J=5.6Hz), 7.39(1H, d, J=5.6Hz), 4.13(2H, t, J=7.4Hz), 1.75(2H, m), 1.41(2H, m), 0.95(3H, t, J=7.3Hz)

EXAMPLE 6
7-(n-Butyl)-6,7-dihydro-4-hydroxy-6-oxo-N-(3-pyridyl)thieno-[2,3-b]pyridine-5-carboxamide (Compound 6)

Compound 6 was obtained (yield: 76%) in a manner similar to Example 3 except for using Compound b obtained in Reference Example 2 in place of Compound a and using 3-aminopyridine in place of 4-aminopyridine.
Melting point: 158.0°–158.4° C.
MS (EI) m/e: 343 (M+)
IR (KBr) cm 1616, 1585, 1561, 1542, 1535, 1482, 752
NMR (DMSO-d$_6$) δ(ppm): 15.87(1H, s), 12.49(1H, s), 8.80(1H, d, J=2.1Hz), 8.37(1H, d, J=3.7Hz), 8.11 (1H, d, J=8.2Hz), 7.39–7.44(1H, m), 7.42(1H, d, J=5.5Hz), 7.35(1H, d, J=5.5Hz), 4.10(2H, t, J=7.5Hz), 1.74(2H, m), 1.40(2H, m), 0.95(3H, t, J=7.3Hz)

EXAMPLE 7
6,7-Dihydro-4-hydroxy-6-oxo-N-(4-pyridyl)thieno[2,3-b]-pyridine-5-carboxamide (Compound 7)

Compound 7 was obtained (yield: 58%) in a manner similar to Example 3 except for using ethyl 6,7-dihydro-4-hydroxy-6-oxothieno[2,3-b]pyridine-5-carboxylate [J. Chem. Res. (S), 214 (1985)]in place of Compound a.
Melting point: >300° C.
MS (EI) m/e. 287 (M+)
IR (KBr) cm$^{-1}$: 1660, 1633, 1573, 1544, 1487, 1426, 1356, 1009, 799, 560, 465
NMR (DMSO-d$_6$) δ(ppm): 15.58(1H, bs), 12.80–12.98(2H, m), 8.51(2H, d, J=6.4Hz), 7.64(2H, d, J=6.4Hz), 7.29(2H, s)

EXAMPLE 8
6,7-Dihydro-4-hydroxy-6-oxo-N-(3-pyridyl)thieno[2,3-b]-pyridine-5-carboxamide (Compound 8)

Compound 8 was obtained (yield: 75%) in a manner similar to Example 3 except for using ethyl 6,7-dihydro-4-hydroxy-6-oxothieno[2,3-b]pyridine-5-carboxylate [J. Chem. Res. (S), 214 (1985)] in place of Compound a, and using 3-aminopyridine in place of 4-aminopyridine.
Melting point: 294.8°–295.9° C.
MS (EI) m/e: 287 (M+)

IR (KBr) cm$^{-1}$: 1648, 1601, 1562, 1482, 1427, 1356, 1263, 801, 554, 472

NMR (DMSO-d$_6$) δ(ppm): 15.85(1H, s), 12.97(1H, s), 12.61(1H, s), 8.80(1H, d, J=2.5Hz), 8.37(1H, dd, J=1.1Hz, 4.7Hz), 8.04-8.13(1H, m), 7.42(1H, dd, J=8.2Hz, 4.5Hz), 7.29(1H, d, J=4.5Hz), 7.29(1H, dd, J=9.9Hz, 5.4Hz)

EXAMPLE 9 Tablet

A tablet having the following ingredients is prepared in a conventional manner.

| | |
|---|---|
| Compound 1 | 50 mg |
| Lactose | 60 mg |
| Potato starch | 30 mg |
| Polyvinyl alcohol | 2 mg |
| Magnesium stearate | 1 mg |
| Tar pigment | trace |

EXAMPLE 10 Syrup

A syrup preparation having the following ingredients is prepared in a conventional manner.

| | |
|---|---|
| Compound 2 | 50 mg |
| Refined sugar | 30 mg |
| Ethyl p-hydroxybenzoate | 40 mg |
| Propyl p-hydroxybenzoate | 10 mg |
| Strawberry flavor | 0.1 cc |

Water is added until the total volume is 100 cc.

REFERENCE EXAMPLE 1 Ethyl 4-(n-butyl)-4,5-dihydro-7-hydroxy-5-oxothieno[3,2-b]-pyridine-6-carboxylate (Compound a)

A) To a solution of 15.7 g (0.100 mol) of methyl 3-aminothiophene-2-carboxylate and 15.2 g (0.110 mol) of potassium carbonate in 200 ml of dimethylformamide was added 34.1 ml (0.300 mol) of n-butyl iodide at 25° C. The mixture was stirred at 120° C. for 10 hours. After cooling, the solvent was evaporated under reduced pressure and 200 ml of ethyl acetate was added to the residue. An inorganic salt was removed by filtration. The filtrate was again concentrated under reduced pressure. The residue was purified by silica gel column chromatography (eluting solvent: ethyl acetate/n-hexane =1/9 v/v) to give 10.2 g (yield: 48%) of methyl 3-(n-butylaminothiophene-2-carboxylate (Compound a-1).

NMR (CDCl$_3$) δ(ppm): 7.35(1H, d, J=5.3Hz), 7.01-7.30 (1H, br), 6.98(1H, d, J=5.3Hz), 3.83(3H, s), 3.28 (2H, m), 1.21-1.88(4H, m), 0.95(3H, t, J=7.5Hz)

B) 10.0 g (46.9 mmols) of Compound a-1 was dissolved in a solvent mixture of 90 ml of 1,2-dichloroethane and 9 ml of 1,4-dioxane. 16.9 ml (0.141 mol) of trichloromethyl chloroformate was dropwise added to the solution at 25° C. The mixture was stirred at 75° C. for 7 hours. After cooling, 0.50 g of activated carbon was added to the reaction mixture followed by reflux for an hour in a nitrogen flow. After cooling, activated carbon was removed by filtration. The filtrate was concentrated under reduced pressure and 15 ml of ethyl acetate and 50 ml of n-hexane were added to the residue. The mixture was then stirred. The precipitated white crystals were filtered and dried to give 6.96 g (yield: of 4-(n-butyl)-5H-thieno[3,2-d]oxazine-5,7(4H)-dione (Compound a-2).

NMR (CDCl$_3$) δ(ppm): 7.95(1H, d, J=5.0Hz), 6.97(1H, d, J=5.0Hz), 4.01(2H, t, J=7.2Hz), 1.17-1.98(4H, m), 0.98(3H, t, J=7.4Hz)

C) Under ice cooling, 552 mg (24.0 mmols) of sodium hydride was added to 67.4 ml (0.444 mol) of ethyl malonate. The mixture was stirred at 25° C. for 30 minutes. To the solution mixture was added 5.00 g (22.2 mmols) of Compound a-2 and the mixture was stirred at 150° C. for an hour. After cooling, 300 ml of water was added to the reaction mixture. The mixture was washed twice with chloroform and 6 N hydrochloric acid aqueous solution was added to the aqueous layer. The precipitated crystals were filtered and dried to give 3.33 g (yield: 51%) of Compound a.

NMR (CDCl$_3$) δ(ppm): 7.69(1H, d, J=5.0Hz), 7.02(1H, d, J=5.0Hz), 4.18(2H, q, J=7.0Hz), 3.64(2H, t, J=7.5Hz), 1.08-1.76(4H, m), 1.22(3H, t, J=7.0Hz), 0.91(3H, t, J=6.1Hz)

REFERENCE EXAMPLE 2 Ethyl 7-(n-butyl)-6,7-dihydro-4-hydroxy-6-oxothieno[2,3-b]-pyridine-5-carboxylate (Compound b)

A) Methyl 2-(n-butyl)aminothiophene-3-carboxylate (Compound b-1) was obtained (yield: 23%) in a manner similar to Reference Example 1,A) step except for using methyl 2-amino-3-thiopenecarboxylate [Chem. Ber., 98, 3571 (1965)] in place of methyl 3-aminothiophene-2-carboxylate.

NMR (CDCl$_3$) δ(ppm): 7.08-7.38(1H, br), 7.03(1H, d, J=5.5Hz), 6.14(1H, d, J=5.5Hz), 3.83(3H, s), 3.23 (2H, q, J=6.2Hz), 1.22-1.90(4H, m), 0.96(3H, t, J=7.4Hz)

B) 7-(N-butyl)-6H-thieno[2,3-d]oxazine-4,6(7H)-dione (Compound b-2) was obtained (yield: 80%) in a manner similar to Reference Example 1,B) step except for using Compound b-1 in place of Compound a-1.

NMR (CDCl$_3$) δ(ppm): 7.59(1H, d, J=5.2Hz), 6.30(1H, d, J=5.2Hz), 3.97(2H, t, J=7.0Hz), 1.15-1.93(4H, m), 0.96(3H, t, J=7.4Hz)

C) Compound b was obtained (yield: 92%) in a manner similar to Reference Example 1,C) step except for using Compound b-2 in place of Compound a-2.

NMR (DMSO-d$_6$) δ(ppm): 7.34(1H, d, J=5.7Hz), 7.29(1H, d, J=5.7Hz), 4.32(2H, q, J=7.0Hz), 3.97(2H, t, J=7.3Hz), 1.60-1.71(2H, m), 1.30(3H, t, J=7.1Hz), 1.26-1.40(2H, m), 0.92(3H, t, J=7.3Hz)

What is claimed is:

1. A thienopyridine derivative represented by formula (I):

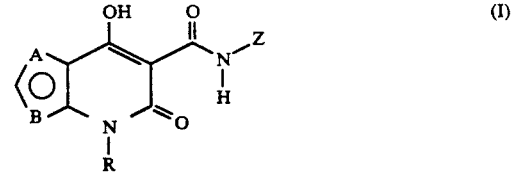

wherein one of A and B represents —S— and the other represents —CH=; R represents hydrogen or lower alkyl, and Z represents pyridyl; or a pharmaceutically acceptable salt thereof.

2. The compound according to claim 1, wherein the lower alkyl is a straight or branched alkyl having 1 to 6 carbon atoms.

3. The compound according to claim 1, wherein A is —S—, and B is —CH=.

4. 4-(n-Butyl)-4,5-dihydro-7-hydroxy-5-oxo-N-(4-pyridyl)thieno[3,2-b]pyridine-6-carboxamide, or a pharmaceutically acceptable salt thereof.

5. A pharmaceutical composition comprising a pharmaceutical carrier and as an active ingredient, an effective amount of the compound as defined by claim 1.

* * * * *

UNITED STATES PATENT AND TRADEMARK OFFICE
CERTIFICATE OF CORRECTION

PATENT NO. : 5,219,864

DATED : June 15, 1993

INVENTOR(S) : FUMIO SUZUKI, ET AL.

It is certified that error appears in the above-identified patent and that said Letters Patent is hereby corrected as shown below:

COLUMN 2

Line 30, "formulas (III):" should read --formula (III):--.
Line 33, "$H_2N-X$" should read --$H_2N-Z$--.
Line 35, "X" should read --Z--.

COLUMN 3

Line 11, "a" should read --an--.
Line 15, "int he" should read --in the--.

COLUMN 4

Line 32, "method" should read --methods--.
Line 43, "Co.." should read --Co.).--.

COLUMN 5

Line 67, "Co" should read --Co:--.

COLUMN 6

Line 43, "pepper mint," should read --peppermint,--.
Line 63, "EXAMPLE 1 5" should read --EXAMPLE 1--.

COLUMN 7

Line 8, "S:" should read --S--.

COLUMN 8

Line 18, "1289," should read --1289, 1229,--.
Line 36, "cm" should read --$cm^{-1}$:--.

UNITED STATES PATENT AND TRADEMARK OFFICE
CERTIFICATE OF CORRECTION

PATENT NO. : 5,219,864
DATED : June 15, 1993
INVENTOR(S) : FUMIO SUZUKI, ET AL.

It is certified that error appears in the above-identified patent and that said Letters Patent is hereby corrected as shown below:

COLUMN 8

Line 51, "m/e." should read --m/e:--.

COLUMN 9

Line 67, "(yield:" should read --(yield: 66%)--.

COLUMN 10

Line 2, "J=5 0Hz)," should read --J=5.0Hz),--.

Signed and Sealed this

Fifteenth Day of March, 1994

BRUCE LEHMAN

*Attest:*

*Attesting Officer*    *Commissioner of Patents and Trademarks*